United States Patent [19]

Hochstrasser

[11] Patent Number: 4,874,490
[45] Date of Patent: Oct. 17, 1989

[54] PRE-CAST GEL SYSTEMS FOR TWO-DIMENSIONAL ELECTROPHORESIS

[75] Inventor: Denis F. Hochstrasser, Geneva, Switzerland

[73] Assignee: Bio-Rad Laboratories, Inc., Hercules, Calif.

[21] Appl. No.: 267,069

[22] Filed: Nov. 4, 1988

[51] Int. Cl.⁴ ............................................. G01N 27/26
[52] U.S. Cl. ............................... 204/182.1; 204/299 R; 204/182.8
[58] Field of Search ............... 204/182.1, 294 R, 182.8

[56]  References Cited
U.S. PATENT DOCUMENTS 4,385,974  5/1983  Shevitz ........................ 204/299 R X
4,443,319  4/1984  Chait et al. ................... 204/182.8 X

FOREIGN PATENT DOCUMENTS 58-140634   8/1983  Japan ................................. 204/182.8
58-193446  11/1983  Japan ................................. 204/182.8
61-288148  12/1986  Japan ................................. 204/182.8

Primary Examiner—John F. Niebling
Assistant Examiner—John S. Starsiak, Jr.
Attorney, Agent, or Firm—Townsend and Townsend

[57] ABSTRACT

A strip gel and a slab gel are combined in a single gel enclosure or on a single gel backing for two-dimensional electrophoresis. The enclosure is comprised of a single pair of support plates, and a removable electrically insulating region is included to separate the gels. The region is occupied either by air or an electrically nonconductive material which can be removed without disturbing either gel. In use, a sample is loaded onto one end of the strip gel and an electric potential is imposed across the strip gel for the first dimension separation while the strip gel is electrically insulated from the slab gel. The insulating region is then removed and the two gels placed in electrical contact for the second dimension separation.

21 Claims, 4 Drawing Sheets

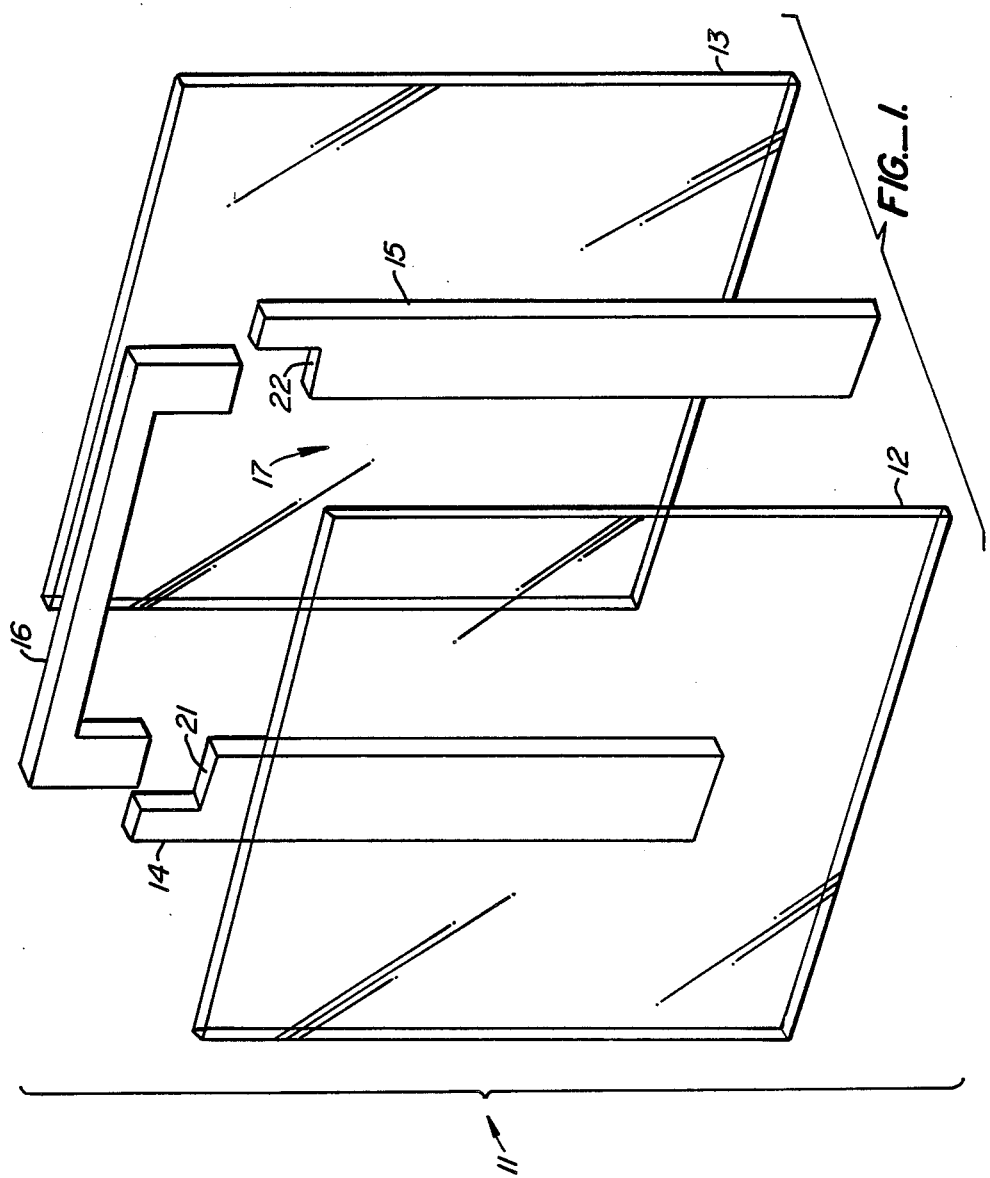

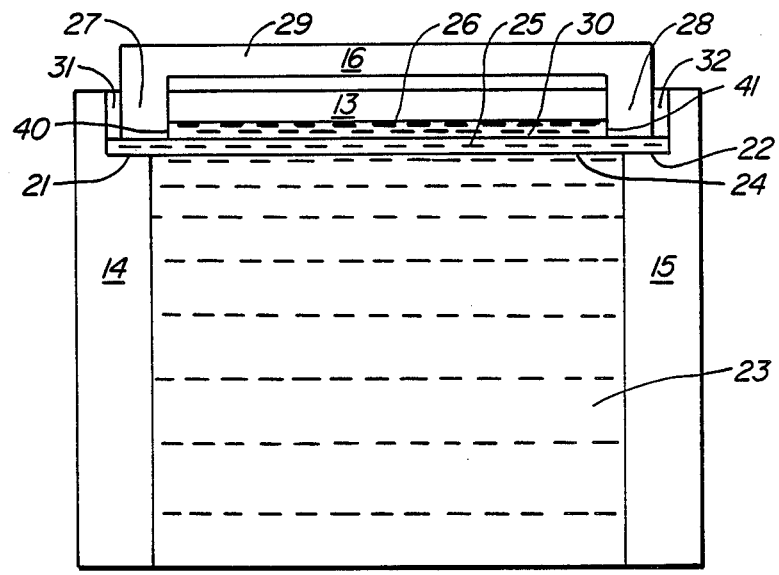
FIG._2.

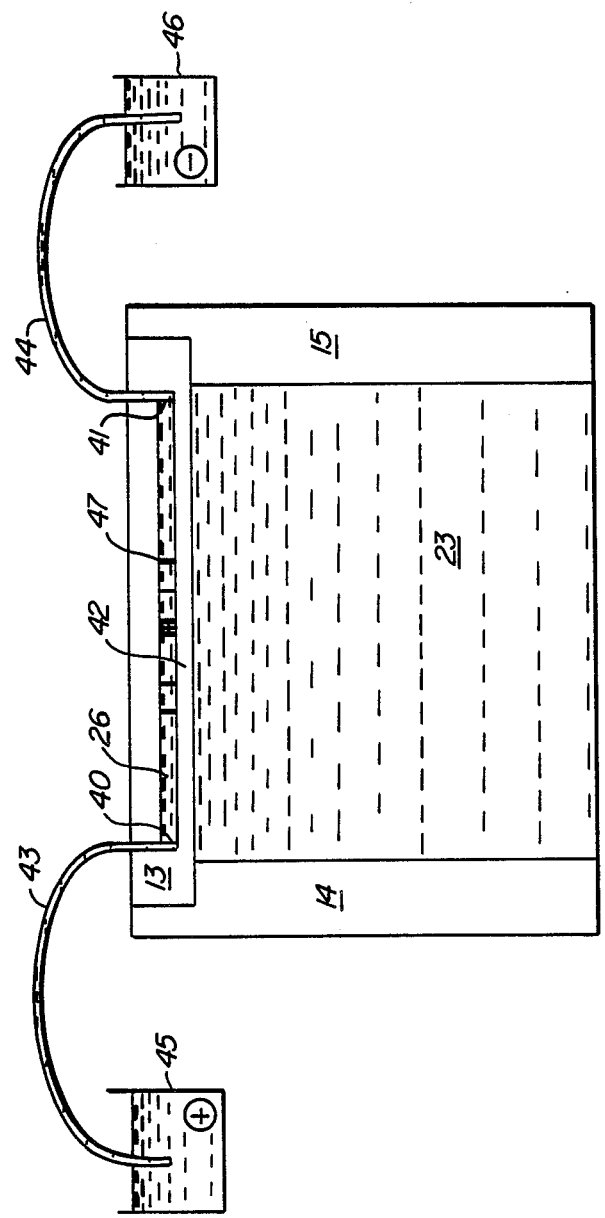
FIG._3.

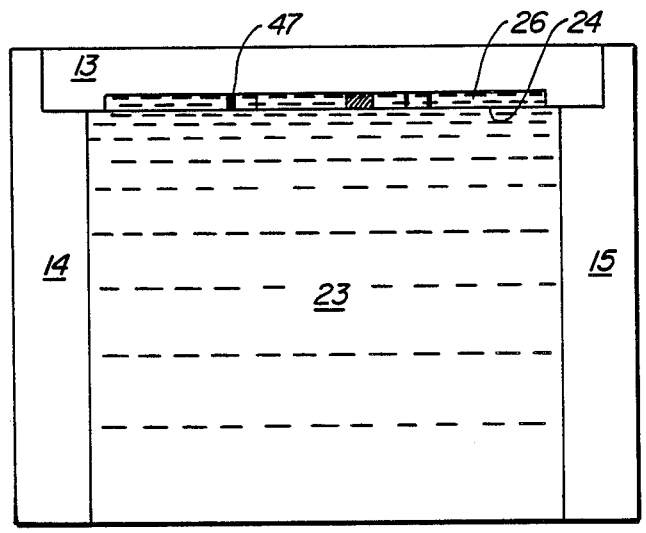
FIG._4a.
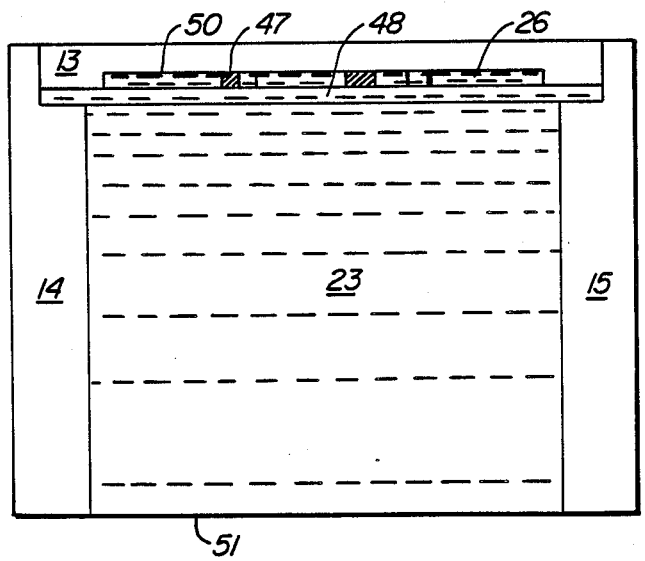
FIG._4b.

PRE-CAST GEL SYSTEMS FOR TWO-DIMENSIONAL ELECTROPHORESIS

This invention relates to two-dimensional gel electrophoresis, and in particular to procedures for preparing and using the gels used in gel separations in two dimensions.

BACKGROUND AND SUMMARY OF THE INVENTION

Two-dimensional electrophoresis is widely used to separate complex protein mixtures. By permitting separation to occur on the basis of two different sets of properties in succession, two-dimensional electrophoresis provides much higher resolving power than that obtainable in a single stage separation.

The technique has been used to combine separation parameters in a variety of ways. Separation based on charge for example has been performed in the first stage, followed by separation based on molecular weight in the second. Likewise, separation in one gel concentration has been followed by separation in another concentration of the same gel. As further examples, two stages have been used to effect a stepwise change in pH, a homogeneous gel followed by a pore gradient gel, the use of two different protein solubilizers or two concentrations of the same solubilizer, a discontinuous buffer system in one stage and a continuous buffer system in the other, and the use of isoelectric focusing followed by homogeneous or pore gradient electrophoresis. Such techniques have permitted the separation of serum or cell proteins, bacterial proteins, non-histone chromatin proteins, ribosomal proteins, mixtures of ribonucleoproteins and ribosomal proteins, nucleic acids, and similar materials.

The basic procedure in a two-dimensional system begins with a first dimension separation in an elongate or rod-shaped gel, such as one having a diameter on the order of 5.0 mm, with migration and separation occurring along the gel axis until the solutes or proteins are distributed among zones positioned along the length of the rod. This is followed by placement of the rod along one edge of a slab gel to effect the second dimension--migration of the solutes from each zone into the slab gel in the direction transverse to the rod gel axis.

The difficulties encountered in procedures of this type are those relating to the transfer of the rod-shaped gels after the first dimension separation has occurred to prepare for the second dimension separation. The first dimension separation generally takes place in the tube in which the rod gel is originally cast. Once the first dimension is complete, the gel rod with the solute zones is removed from the tube by physical means such as extrusion, then placed along the exposed edge of the slab gel. These manipulations require delicate handling, and even with the exercise of a great deal of care, there remains the risk of damage to the gel and distortion or disturbance of the solute zones. Once extracted, the rod gel must be properly aligned with the slab gel, and placed in full contact for purposes of both electrical continuity and unobstructed solute migration between the gels. These are further sources of error and lack of reproducibility. In addition to the handling difficulties and potential for inaccuracies and lack of reproducibility, the time required in the handling and placement of the rod gel is detrimental to operator efficiency, and any fatal errors will result in irretrievably lost time and data.

Some have used gel strips for the first dimension separation, but similar difficulties, errors and lack or reproducibility have been encountered.

The present invention resides in a pre-cast twodimensional gel system, with the first and second dimension gels combined on a single gel support in which both stages of the separation take place. The support may be an enclosure comprising a single pair of plates, with appropriate spacers to set the spacing between the plates and define the gel thicknesses. Both first and second dimension gels are cast and retained between the plates. The second dimension gel is a slab occupying a portion of the space between the plates, while the first dimension is a strip positioned in the remaining space, parallel to the slab, with a removable electrically insulating layer separating the gels. Alternatively, the support may be gel backing comprised of a sheet of plastic, gel bond or other supporting material on which both first and second dimension gels are cast, with the insulating layer, which may be a layer of insulating material or an air space, between them.

The first dimension separation is thus performed by loading the sample on one end of the strip gel and imposing an electric field across the strip gel in the lengthwise direction while the two gels are electrically insulated from each other, then removing the electrically insulating layer and placing the two gels in electrical contact along their full length, followed by imposing an electric field across both in a direction transverse to the first. The electrically insulating layer may be solid, liquid or gas, and electrical contact between the two gels for the second dimension separation maybe achieved either by direct contact or by the insertion of an electrically conductive layer. The invention eliminates the need for transferring a rod or strip gel from one support enclosure to another between the two stages of the separation, thereby lessening the risk of gel damage and zone distortion and lowering the incidence of inaccuracies and systematic error.

Further objects, advantages and features of the invention will be apparent from the description which follows.

BRIEF DESCRIPTION OF THE DRAWINGS

FIG. 1 is an exploded perspective view of a gel enclosure suitable for use in casting and retaining gels in accordance with the present invention FIG. 2 is a front view of a two-dimensional gel system prepared in the gel enclosure of FIG. 1, with one support plate removed, immediately following the casting of the second dimension gel.

FIG. 3 depicts the gel system of FIG. 2, again with one of the plates removed, during the first stage of the separation.

FIGS. 4a and 4b depict the gel system of FIGS. 2 and 3 in condition for the start of the second stage.

DETAILED DESCRIPTION OF THE INVENTION AND PREFERRED EMBODIMENTS

In accordance with the present invention, an elongate gel in the form of a strip is used for the first dimension separation, in place of the rod-shaped gel or separate gel strip of the prior art. The strip gel is cast between the support plates in the same manner as the slab gel, as a shallow layer above the slab gel. This is preferably done after the slab gel has been formed. The insulating layer between the two may be solid, liquid or gas, and is either present during the casting of the strip gel in which case it also serves as a barrier preventing fluid contact between the two gels, or is substituted for the barrier layer once the strip gel is cast.

The various layers and the gel enclosure are shaped and sized in such a way that the insulating layer can be removed once the first dimension separation is complete. This is generally done by providing an open passage communicating the region of the insulating layer with the exterior of the gel enclosure. The passage is preferably in the form of a clearance around one or both ends of the strip gel, where the insulating layer can be either drawn off or forced outward by displacement.

The drawings herewith provide a detailed view of one illustrative embodiment of the invention.

FIG. 1 depicts a gel enclosure 11 in exploded form, suitable for use in casting and using the gels for both stages of the electrophoresis. The components of the enclosure include two glass plates 12, 13, a pair of lateral spacers 14, 15 and an upper spacer 16. The lateral spacers 14, 15, as in conventional slab gel enclosures, set the spacing between the glass plates 12, 13, and thus establish the thickness of the gels to be cast between the plates. The lateral spacers shown in the drawing are of uniform thickness, resulting in gels of likewise uniform thickness. Alternatively, lateral spacers with thicknesses varying along the spacer lengths may be used, such as wedge-shaped spacers, for the purpose of varying the gel thickness in the vertical direction.

The lateral spacers 14, 15 and glass plates 12, 13 are held together in a sandwich-type arrangement by clamps (not shown) along each side. A gel solution is poured into the space 17 between the glass plates and lateral spacers and permitted to solidify into a gel according to conventional procedures, with the enclosure mounted vertically in a casting stand (not shown). Suitable clamps casting stands and other equipment required for forming the gel are conventional and widely used and available in the industry.

The lateral spacers 14, 15 are fixed in position by the clamps. The upper spacer 16 however is removable, and is used during casting of the strip gel. Its use is more clearly seen by reference to FIG. 2.

In FIG. 2, the forward glass plate 12 of FIG. 1 has been omitted for purposes of clarity. Remaining in view are the rear glass plate 13, the two lateral spacers 14, 15 and the removable upper spacer 16.

Referring back to FIG. 1, it will be noted that the lateral spacers 14, 15 are each provided with shoulders 21, 22 facing toward the interior space 17. In this embodiment, these shoulders mark the liquid level for pouring the solution from which the slab gel 23 (FIG. 2) will be formed. The upper edge 24 of the slab gel is thus coplanar with these shoulders. To cast the slab gel, the gel enclosure 11 is assembled without inclusion of the upper spacer 16, and the gel solution is poured in to the level of the shoulders 21, 22 and solidified.

Once the slab gel 23 is fully formed, a protective layer 25 is placed over it, sealing it supper edge 24. This protective layer may vary in form and composition, as explained further below. In each of its various forms, however, it will be of a material into which the gel forming solution used for the strip gel 26 to be placed above it will not diffuse. The upper spacer 16 is inserted between the glass plates and placed in the position shown. The strip gel solution is then added to form a layer above the protective layer 25, with the protective layer substantially preventing all contact between the strip gel solution and the slab gel 23.

The upper spacer 16 is comprised of two lets 27, 28 depending downward from each end of the spacer, connected by a central crossbar 29. The upper spacer 16 is inserted far enough so that the legs 27, 28 extend to the interface 30 between the protective layer 25 and the strip gel solution 26, leaving a discontinuity in the strip gel solution layer at either side. In the embodiment shown in the drawing, it will be noted that small clearances 31, 32 are left between the legs 27, 28 of the upper spacer and the portions of the lateral spacers 14, 15 above the shoulders 21, 22. These clearances serve no function other than to enhance the ease of insertion and withdrawal of the upper spacer 24 without disturbing the lateral spacers 14, 15. Once the upper spacer 16 is in place, the strip gel solution in these clearance areas may be aspirated off or simply allowed to remain.

With the upper spacer in place as shown in FIG. 2, the strip gel solution is permitted to solidify into a gel. Once the gel is fully formed, the upper spacer 16 is removed. The protective layer 25 may then be either removed itself, or left in place provided that it is electrically insulating. The aim in either case is to leave between the two gels in intervening barrier electrically insulating one gel from the other. If the protective layer 25 is in liquid form, it may be poured off or aspirated off, leaving an air space between the two gels. For example, with aqueous gels, the protective layer may be a nonpolar liquid substantially immiscible with either the gels or the gel-forming solutions. Chloroform and other nonpolar organic solvents or oils which are heavier than water may be used in this regard. Alternatively, the protective layer may be a lowmelting solid, preferably one with a melting temperature within the range of about 25° C. to about 75° C. Such a material may be poured over the upper edge 24 of the slab gel in liquid form, then cooled and thus permitted to solidify before the strip gel solution is added. Once the latter has solidified, the system is reheated to heat the protective layer above its melting point once again, returning it to liquid form so that it may be poured or aspirated off. Methyl stearate and other substances with boiling points within this range are suitable for such a procedure. A further alternative is the use of a solid or polymer which is dissolvable in solvents other than water. Removal of the material is thus effected by adding an appropriate solvent and pouring off the resulting solution. A still further alternative is the use of a flexible solid material such as a strip of rubber, which can be placed over the top of the slab gel prior to the pouring of the strip gel solution, then pulled out once the strip gel solution has solidified and the upper spacer 16 is removed. The rubber or other solid material must of course be wide enough to laterally seal against both glass plates to prevent contact between the slab gel and the strip gel solution.

As mentioned above, if the protective layer 25 is made of a material which is electrically insulating in addition to its ability to prevent mixing between the strip gel solution and the slab gel, it may be left in place. The result will be a solid or liquid insulating layer rather than air. In either case, the result will be a barrier to the transmission of an electric current between the two gels and any electric potential imposed across the strip gel from one end to the other will exert its full effect in the strip gel itself. The removal of the upper spacer 16 leaves the two ends 40, 41 of the strip gel 26 exposed, thereby facilitating their connection to electrode buffers to permit the electrophoretic separation to take place.

FIG. 3 offers a depiction of one method of performing the first stage electrophoresis. In this embodiment, the protective layer 25 has been removed, the exposed edges of the gels dried with air, and the intervening space 42 occupied by air. Strips 43, 44 of absorbent material, moistened with electrolyte solution are placed in contact with the two ends 40, 41 respectively of the strip gel 26. The opposite end of each strip is immersed in electrolyte reservoirs 45, 46, across which an electric potential is imposed by conventional means.

The sample to be separated may be loaded onto the strip gel 26 by any conventional means. For example, the sample may be placed at the end of one of the two absorbent strips 43, 44, prior to the latter being placed in contact with the strip gel 26. The first stage electrophoresis is then permitted to occur, with the solutes migrating in the longitudinal direction of the strip gel to form zones 47 spaced along the strip gel 26 as shown.

Once the desired degree of separation in the first dimension has occurred, the two gels are placed in electrical contact so that the solutes in any single zone will separate from each other. FIGS. 4a and 4b demonstrate alternative ways of achieving this. In FIG. 4a, the strip gel 26 has been physically pushed down until it fully contacts the slab gel 23 with the upper edge 24 of the slab gel now forming the interface between the two gels. Care is taken to avoid the entrapment of air bubbles between the two gels.

In FIG. 4b, the strip gel 26 is left in its original position, and a new intervening gel 48 is formed between it and the slab gel 23. This intervening gel 48 is formed of a material which is both electrically conductive and capable of permitting the migration of solutes through it to enter the slab gel 23. This intervening gel may be formed by pouring an appropriate gel-forming solution into the gel enclosure on either side of the strip gel 236 until it reaches or surpasses the lower surface of the strip gel, and upon solidification provides full contact between the two gels with no air bubbles entrapped. The intervening gel 48 may be of the same material as the slab gel, or any other material which will produce these results.

The procedures described above are equally applicable to gels polymerized on a plastic backing or gel bond.

Once the electrical connection has been made between the strip gel 26 and the slab gel 23, the upper edge 50 of the strip gel and the lower edge 51 of the slab gel are placed in contact with electrode buffers for the performance of the second stage electrophoresis, resulting in downward migration from the strip gel into the slab gel. This may be accomplished by the use of conventional slab electrophoresis cells, widely available commercially and well known to those skilled in the art. An example of one such cell is that disclosed in U.S. Pat. No. 4,575,040, incorporated herein by reference. Once the desired degree of separation in the second dimension has occurred, the slab gel is removed from the enclosure and processed for analysis according to conventional methods. These generally include staining and drying of the gel, followed by either quantitative or qualitative measurement of the resulting solute pattern.

The gels used in accordance with the present invention may be any combination of gels suitable for use in two-dimensional electrophoretic separations. The gels will generally be aqueous gels, including polyacrylamide gels, starch gels, agar gel and the like, utilizing various gel concentrations and porosities, homogeneous in concentration or gradient, constant or gradient pH, with or without solubilizers or with solubilizers of varying types and concentrations, and with continuous or discontinuous buffer systems. Among the various applications to which these systems can be put are separations where the first dimension is isoelectric focusing and the second is a constant pH electrophoresis. The system also finds utility in separations where the first dimension is done in the presence of urea. Polyacrylamide gels cross linked with cross linking agents of the following formula are particularly useful in this regard:

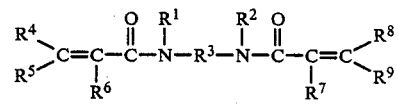

in which:

$R^1$, $R^2$ and $R^3$ are defined such that $R^1$ and $R^2$ are independently $C_1$–$C_5$ alkyl, and $R^3$ is $C_1$–$C_8$ alkylene; or $R^1$ and $R^2$ are joined to form $C_1$–$C_8$ alkylene, and $R^3$ is $C_1$–$C_8$ alkylene; or $R^1$ is joined to $R^3$ to form a saturated hydrocarbyl group of 3 to 10 carbon atoms which together with the N atom to which $R^1$ and $R^3$ are joined forms a N-containing ring, and $R^2$ is $C_1$–$C_5$ alkyl; or $R^1$ and $R^2$ are joined to $R^3$ to form a saturated hydrocarbyl group of 7 to 15 carbon atoms which together with the N atoms forms two N-containing rings; and $R^4$, $R^5$, $R^6$, $R^7$, $R^8$, and $R^9$ are independently selected from the group consisting of H and $C_1$–$C_5$ alkyl.

In a particularly useful system, the strip gel is a polyacrylamide gel cross linked with diacrylylpiperazine, and contains urea in a protein-solubilizing amount, and the slab gel, which may also be polyacrylamide cross linked with diacrylylpiperazine, contains sodium dodecyl sulfate in a protein-solubilizing amount in place of or in addition to the urea.

The term "protein-solubilizing amount" in either case is used herein to denote any amount which will render the proteins in the sample soluble in an aqueous phase. In the case of urea, the amount will generally range from about 2M to about 25 M, preferably from about 8M to about 10M. In the case of sodium dodecylsulfate, the amount will generally range from about 0.03% to about 3% by weight. Further solubilizers include formamide and acetic acid. Selection of the appropriate solubilizer and its optimal amount will vary depending on the nature of the proteins or solutes being separated and their concentration in the sample, and are well within the routine skill of those skilled in the art.

The foregoing is offered primarily for purposes of illustration. It will be readily apparent to those skilled in the art that variations, modifications and substitutions in the materials, procedures, and operating conditions described herein may be made without departing from the spirit and scope of the invention.

What is claimed is:

1. A pre-cast two-dimensional electrophoresis gel system comprising a first gel in the form of an elongate strip and a second gel in the form of a slab, said first and second gels retained on a single gel support means and spaced apart thereon from one another by a nonconductive flexible solid.

2. A pre-cast two-dimensional electrophoresis gel system comprising a first gel in the form of an elongate strip and a second gel in the form of a slab, said first and second gels retained on a single gel support means and spaced apart thereon from one another by a strip of rubber.

3. A pre-cast two-dimensional electrophoresis gel system comprising a first gel in the form of an elongate strip and a second gel in the fomr of a slab, said first and second gels retained on a single gel support means and spaced apart thereon from one another by a nonconductive material which is solid at room temperature and has a melting point between about 25° C. and about 75° C.

4. A pre-cast two-dimensional electrophoresis gel system comprising a first gel in the form of an elongate strip and a second gel in the form of a slab, said first and second gels retained on a single gel support means and spaced apart thereon from one another by a nonconductive material which is solid at room temperature and is solubel at room temperature in a nonaqueous solvent.

5. A pre-cast two-dimensional electrophoresis gel system in accordance with claim 3 in which said nonconductive material has a melting point between about 30° C. and about 50° C.

6. A pre-cast two-dimensional electrophoresis gel system in accordance with claim 3 in which said nonconductive material is methyl stearate.

7. A pre-cast two-dimensional electrophoresis gel system in accordance with claims 1, 2, 3 or 4 in which said gel support means is comprised of a pair of substantially parallel support plates.

8. A pre-cast two-dimensional electrophoresis gel system in accordance with claims 1, 2, 3 or 4 in which said gel support means is comprised of a pair of substantially parallel support plates, and said first and second gels are arranged between said support plates to leave an open passage to permit removal of said removable electrically insulating layer from said support plates without disturbing said first and second gels.

9. A pre-cast two-dimensional electrophoresis gel system in accordance with claims 1, 2, 3 or 4 in which said first gel contains urea in a protein-solubilizing amount, and said second gel contains sodium dodecyl sulfate in a protein-solubilizing amount.

10. A pre-cast two-dimensional electrophoresis gel system in accordance with claims 1, 2, 3 or 4 in which said first and second gels are polyacrylamide gels, said first gel contains urea in a protein-solubilizing amount, said second gel contains sodium dodecyl sulfate in a protein-solubilizing amount, and said polyacrylamide in said first gel is cross linked with a compound having the formula

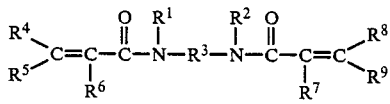

in which:

$R^1$, $R^2$ and $R^3$ are defined such that $R^1$ and $R^2$ are independently $C_1$-$C_5$ alkyl, and $R^3$ is $C_1$-$C_8$ alkylene; or $R^1$ and $R^2$ are joined to form $C_1$-$C_8$ alkylene; or $R^1$ is joined to $R^3$ to form a saturated hydrocarbyl group of 3 to 10 carbon atoms which together with the N atom to which $R^1$ and $R^3$ are joined forms a N-containing ring, and $R^2$ is $C_1$-$C_5$ alkyl; or $R^1$ and $R^2$ are joined to $R^3$ to form a saturated hydrocarbyl group of 7 to 15 carbon atoms whic together with the N atoms forms two N-containing rings; and $R^4$, $R^5$, $R^6$, $R^7$, $R^8$, nd $R^9$ are independently selected from the group consisting of H and $C_1$-$C_5$ alkyl.

11. A pre-cast two-dimensional electophoresis gel system in accordance with claims 1, 2, 3 or 4 in which said first and second gels are polyacrylamide gels, said first gel contains urea in a protein-solubilizing amount, said second gel contains sodium dodecyl sulfate in a protein-solubilizing amount, and said pllyacrylamide in said first gel is cross linked with diacrylylpiperazine.

12. A method for casting a two-dimensional electrophoresis gel, said method comprising:

(a) forming a first gel in the form of a slab on a gel support; leaving an empty space on said support along an exposed edge of said slab;

(b) forming a second gel in said empty space in the form of an elongate strip separated from said first gel by a removable nonconductive solid.

13. A method in accordance with claim 12 in which step (b) comprises:

(i) placing a nonconductive solid in said empty space adjacent to said exposed edge of said slab;

(ii) placing a gel-forming liquid in said empty space to form a second layer adjacent to said first layer; and (iii) forming said second layer into a gel.

14. A method in accordance with claim 13 in which said nonconductive solid is a strip of flexible material.

15. A method in accordance with claim 13 in which said nonconductive solid is a strip of rubber.

16. A method in accordance with claim 13 in which said nonconductive solid has a melting point between about 25° C. and about 75° C.

17. A method in accordance with claim 16 in which said gel support is a pair of support plates arranged parallel to each other, and step (a) comprises forming said gel between said support plates, and said empty space is between said support plates.

18. A method for casting a twodimensional electrophoresis gel, said method comprising:

(a) forming a first gel between a pair of support plates, leaving an empty space between said support plates along an exposed edge of said first gel;

(b) placing a nonconductive material in said empty sapce to form a first layer adjacent to said exposed edge of said slab, said nonconductive material being one which is a solid at room temperature as has a melting point between about 25° C. and about 75° C.;

(c) placing a gel-forming liquid in said empty space to form an elongate second layer adjacent to said first layer, said substance and said gel-forming liquid being substantially immiscible;

(d) forming said second layer into an elongate gel; and (e) heating said nonconductive material to a temperature at or above said melting point and removing sid substance in the liquid state from said support plates.

19. A method in accordance with claim 18 in which step (b) comprises forming said first layer while said nonconductive material is heated to liquid form followed by cooling said substance to solid form.

20. A method for separating a sample into components by two-dimensional electrophoresis, said method comprising:
  (a) providing a two-dimensional electrophoresis gel arrangement comprising a first gel in the form of an elongate strip having an elongate dimension and a second gel in the form of a slab, said first and second gels retained on a single gel support means, and said first and second gels separated by an intervening region of a material which is solid at room temperature and has a melting point between about 25° C. and about 75° C.;
  (b) loading said sample onto said first gel at one end thereof;
  (c) imposing an electric field across said first gel in a direction parallel to said elongate dimension, to effect electroporetic seaparation therein of said components of said sample into zones;
  (d) heating said nonconductive material above said melting point;
  (e) removing said nonconductive material while in the liquid state; and
  (f) moving said first gel toward said second gel to place said first and second gels in direct contact; and
  (g) imposing an electric field across both said first and second gels in a direction transverse to said elongate dimension, to effect electrophoretic separation of said zones in said second gel.

21. A method for separating a sample into components by two-dimensional electrophoresis, said method comprising:
  (a) providing a two-dimensional electrophoresis gel arrangement comprising a first gel in the form of an elongate strip having an elongate dimension and a second gel in the form of a slab, said first and second gels retained on a single gel support means, and said first and second gels separated by an intervening region of a material which is solid at room temperature an dhas a melting point between about 25° C. and about 75° C.;
  (b) loading said sample onto said first gel at one end thereof;
  (c) imposing an electric field across said first gel in a direction parallel to said elongate dimension, to effect electrophoretic separation therein of said components of said sample into zones;
  (d) heating said nonconductive material above said melting point;
  (e) replacing said nonconductive material while in the liquid state with an electrically conductive gel-forming liquid;
  (f) forming said gel-forming liquid into an electrically conductive gel; and
  (g) imposing an electric field across both said first and second gels in a direction transverse to said elongate dimension, to effect electrophoretic separation of said zones in said second gel.

* * * * *